United States Patent [19]

Knapp et al.

[11] Patent Number: 5,393,523
[45] Date of Patent: Feb. 28, 1995

[54] *PLASMODIUM FALCIPARUM* VACCINE COMPRISING A RECOMBINANT HISTIDINE-RICH PROTEIN-HRP-II

[75] Inventors: Bernard Knapp, Marburg-Schröck; Erika Hundt, Marburg-Wehrshausen; Burkhard Enders; Hans Kupper, both of Marburg, all of Germany

[73] Assignee: Behringwerke Aktiengesellschaft, Marburg/Lahn, Germany

[21] Appl. No.: 109,478

[22] Filed: Aug. 20, 1993

Related U.S. Application Data

[63] Continuation of Ser. No. 265,442, Nov. 1, 1988, abandoned.

[30] Foreign Application Priority Data

Nov. 3, 1987 [DE] Germany .............................. 3737238

[51] Int. Cl.⁶ .................... A61K 35/66; A61K 39/015
[52] U.S. Cl. .................................... 424/191.1; 514/2; 514/12; 435/69.3; 530/324; 530/350; 530/395; 530/855; 424/268.1
[58] Field of Search ....................... 514/2, 12; 424/88; 530/350, 395, 324, 855; 435/69.3

[56] References Cited

U.S. PATENT DOCUMENTS 4,721,617 1/1988 Johnson .
5,130,416 7/1992 Wellems .............................. 530/350

OTHER PUBLICATIONS

Groux et al., "Functional Characterization of the Antibody–Mediated Protection Against Blood Stages of *Plasmodium falciparum* in the Monkey *Saimiri sciureus*", Eur. J. Immunol., 20:2317–2323 (1990).

Gysin et al., "Characterization by Anti–Ig–Monoclonal Antibodies of Protective and Non–Protective Antibodies Against Asexual Forms of *Plasmodium falciparum* in the Saimiri Monkey", Ann. Inst. Pasteur/Immunol., 138:829–844 (1987).

Knapp et al., "A New Blood Stage Antigen of *Plasmodium falciparum* Transported to the Erythrocyte Surface", Molecular and Biochemical Parasitology, 37:47–56 (1989).

"Role of non–human primates in malaria vaccine development: Memorandum from a WHO Meeting", Bulletin of the WHO, 66:719–728 (1988).

Patarroyo et al., "Induction of Protective Immunity Against Experimental Infection . . . ", Nature, 328:629–632 (1987).

Patarroyo et al., "A Synthetic Vaccine Protects Humans Against Challenge with Asexual Blood . . . ", Nature, 332:158–161 (1988).

Lenstra et al., "Cloning and Sequencing of *Plasmodium falciparum* DNA Fragments . . . ", Biochemical and Biophysical Res. Comm., 146:368–377 (1987).

H. D. Stahl et al., Nucl. Acids. Res., 13, (1985), pp. 7837–7846.

T. Maniatis et al., Molecular Cloning, A Laboratory Manual, (1982), Table of Contents.

H. Kupper et al., Proceedings of the Fourth International Symposium of Genetics of Industrial Microorganisms, (1982), pp. 222–226.

F. Sanger et al., Proc. Natl. Acad. Sci., 74, (1977), pp. 5463–5467.

(List continued on next page.)

Primary Examiner—Christine M. Nucker
Assistant Examiner—Thomas Cunningham
Attorney, Agent, or Firm—Finnegan, Henderson, Farabow, Garrett & Dunner

[57] ABSTRACT

Recombinant histidine-rich protein of *Plasmodium falciparum*, its preparation and use. It was possible, by screening two different *Plasmodium falciparum* cDNA gene banks with an antiserum against a 41 kD protein and by cross-hybridization with the insert DNA of a clone obtained therewith, to isolate a gene which codes for a Histidine-Alanine-rich protein (HRP-II). This protein protects aotus monkeys from infection with *P. falciparum* and is thus a suitable constituent of a malaria vaccine.

2 Claims, 3 Drawing Sheets

OTHER PUBLICATIONS

T. Huynh et al., DNA Cloning, vol. 1, (1985), pp. 49–78.
K. Strebel et al., J. of Virology, 57, (1985), pp. 983–991.
A. M. Maxam et al., Meth. Enzymol, 65, (1980), pp. 499–560.
G. Pasvol et al., Ann. Trop. Med. Parasitol, 72, (1978), pp. 87–88.
C. Lambros et al., J. Parasitol, 65, (1979), pp. 418–420.
W. Trager et al., Science, 193, (1976), pp. 673–675.
E. Remaut et al., Gene, 22, (1983), pp. 103–113.
L. H. Perrin et al., J. Clin. Invest., 75, (1985), pp. 1718–1721.
A. Cheung et al., The EMBO Journal, 4, (1985), pp. 1007–1012.
R. J. Howard et al., J. Cell. Biol., 103, (1986), pp. 1269–1277.
T. Wellems et al., Proc. Natl. Acad. Sci., 83, (1986), pp. 6065–6069.
Godson, G. N., Scientific American, May 1985, Molecular Approaches to Malaria Vaccines.

FIG.2

PLASMODIUM FALCIPARUM VACCINE COMPRISING A RECOMBINANT HISTIDINE-RICH PROTEIN-HRP-II

This application is continuation of application Ser. No. 07/265,442, filed Nov. 1, 1988, now abandoned.

Because of the increasing resistance both of the malaria parasite Plasmodium falciparum (P. falciparum) to well-tried and newly developed chemotherapeutics and prophylactics, and of its vector (certain species of mosquitoes) to insecticides, malaria has become the main health problem in developing countries. The development of recombinant proteins or synthetic peptides for use in prophylactic vaccination is therefore of great importance. An important step in the development of a modern vaccine is the identification of protective antigens. Antigens are generally classified as protective when they have yielded, in in vivo experiments in an animal model, such as, for example, in saimiri or aotus monkeys, protection from intravenous infection with P. falciparum. To date, all the described attempts at protection of humans have been unsatisfactory, but several isolated P. falciparum proteins have shown a complete or partial protective action in an animal model. This applies both to protein bands of 75 kD and 100 kD purified by gel electrophoresis and to the protein fractions of molecular weights 200 kD, 140 kD and 41 kD purified by gel electrophoresis.

Since it would probably be impossible to prepare from parasite cultures the amounts of antigens required for a vaccine, it is likely that the only suitable method of preparation of such antigens will be by genetic manipulation. Moreover, intolerance of the vaccine resulting from contamination with host cells (erythrocytic constituents) can be ruled out where preparation is based on genetic manipulation.

Of the proteins hitherto prepared by genetic manipulation, a partial protective action has been shown in immunization experiments with saimiri or aotus monkeys by one recombinant expression protein of the 5' repeat region of the so-called RESA 155 kD merozoite protein and one synthetic oligopeptide of the 200 kD merozoite surface precursor protein as well as a combination of synthetic oligopeptides of P. falciparum proteins of molecular weight 200 kD, 55 kD and 35 kD.

The object of the present invention is to find other P. falciparum antigens which can be prepared by genetic manipulation and have a good protective action, because it is highly probable that a mixture of several suitable P. falciparum antigens will be necessary for adequate immunization.

On attempting to clone the abovementioned protective 41 kD antigen with the aid of a monospecific antiserum against this 41 kD protein band there was isolated from a cDNA expression bank a clone 41-3 whose sequence is depicted in Tab. 1. Surprisingly, this sequence codes for a histidine/alanine-rich protein of 21 kD which is comparable with the SHARP or PfHRPII protein described for other Plasmodium strains (H. D. Stahl et al. (1985), Nucl. Acids Res. 13, 7837-7846; T. E. Wellems and R. J. Howard (1986), Proc. Natl. Acad. Sci U.S.A. 83, 6065-6069). Since it was not possible to bring about satisfactory expression of the insert of the clone 41-3, its sequence was used to screen another cDNA gene bank.

From this resulted, by cross-hybridization, a clone λgt10-41-3, and it is was possible to bring about expression of its insert.

The DNA sequence of this clone, which is described hereinafter (Tab. 2), has an open reading frame which terminates with the TAA stop codon in position 568. A very extensive repeat region (nucleotides 1 to 540) codes almost exclusively for histidine, alanine and aspartic acid residues. The basic units of the repeats are formed by Ala-His-His and Ala-Ala-Asp tripeptide repeats.

The Latter repeat units shows slight variability: besides 13 Ala-Ala-Asp tripeptides there are three Ala-Ala-Tyr, two Ala-Ser-Asp, two Ala-Thr-Asp and one Val-Ala-Asp tripeptide units. The Last of these units is a dipeptide lacking the aspartic acid residue.

In contrast, the Ala-His-His tripeptide repeats are highly conserved. Variability exists here only in the number and arrangement of these tripeptides. These are found as monomers (10), dimers (12) and trimers (2) between the Ala-Ala-Asp tripeptides which always occur as monomers.

The sequence presented here is very similar to that of the histidine-rich PfHRPII antigen (T. E. Wellems and R. J. Howard (Loc. cit.)). Comparison of the nucleotide sequences reveals a 90% degree of homology (Tab. 3). The two sequences have an identical 3' end composed of 80 nucleotides but differ in the repeat region as a result of deletions and base exchanges.

Both antigens have a high proportion of the amino acids histidine, alanine and aspartic acid and have the tripeptide repeats Ala-His-His and Ala-Ala-Asp. Differences between the two sequences exist mainly in the arrangement and the number of repeat units. Thus, in the amino acid sequence derived from clone lambda gt-41-3 the nonapeptide repeat Ala-His-His-Ala-His-His-Ala-Ala-Asp predominates over the hexapeptide repeat Ala-His-His-Ala-Ala-Asp; in the PfHRPII antigen in contrast, the proportion of hexapeptide is larger. In general, multimers of the Ala-His-His tripeptide units are more frequent in the sequence described here, compared with the corresponding monomers which are more frequent in PfHRPII.

Nevertheless the insert of clone lambda gt 10-41-3 seems to code for an HRPII antigen which is heterogeneous in different P. falciparum strains. This follows also from a Western Blot analysis with antisera directed against a fusion protein which is coded by the vector pEX 31b-41-3. These sera react with several protein bands in between 70 kD and 50 kD in a decreasing intensity which may be explained by proteolytic degradation of a 70 kD antigen. The molecular weight of the HRPII is between 70 kD and 75 kD depending on the P. falciparum strain. At the same time a protein of 37 kD reacts, whereby here it is probably the homologous HRPIII antigen. A similar Western Blot pattern was observed with antisera against the HRPII antigen by Rock et al. (Rock et al., (1987) Parasitology 95, 209–227). Expression of the nucleotide sequence, which is described above, of the lambda gt10-41-3 clone was brought about as a fusion protein in E. coli.

It was possible in a vaccination experiment with the purified expression product to protect aotus monkeys from P. falciparum infection.

Consequently, the invention relates to a) a method for the preparation, by genetic manipulation, of the HRPII antigen (strain SGE2), b) the gene necessary for this, including its transcription products, c) DNA structures and vectors which contain this gene in whole or in part, d) pro- or eukaryotic cells transformed with such DNA, and the polypeptide expressed by these cells, e) amino acid sequences of this HRPII antigen, oligopeptides and antibodies obtained therewith, and the use thereof for the isolation of polypeptides, as well as the use of *P. falciparum* HRPII for immunization and for diagnosis of malaria, f) vaccines against malaria which contain this amino acid sequence alone or in combination.

Further embodiments of the invention are detailed in the examples which follow and in the patent claims.

EXAMPLE 1

Screening of a cDNA Expression Bank with a Monospecific 41 kD Serum

A cDNA expression bank of the *P. falciparum* strain SGE2 (A. Cheung et al. (1985), The EMBO Journal 4, 1007–1012) was screened by the method of A. Cheung et al. (loc. cit.) with a polyclonal antiserum against a 41 kD protein band purified by gel electrophoresis (L. H. Perrin et al. (1985), J. Clin. Invest. 75, 1718–1721). 3 clones resulted from this, 41-1, 41-2 and 41-3, of which the clone 41-3 was further characterized.

EXAMPLE 2

Sequencing of the Insert of the Clone 41-3

The DNA sequencing was carried out by the method of Maxam and Gilbert (A. Maxam and W. Gilbert (1980), Meth. Enzymol. 65, 499). The DNA sequence and the amino acid sequence derived therefrom are depicted in Tab. 1.

EXAMPLE 3

Isolation and Sequencing of the Clone λgt10-41-3

Since the expression of the insert of the clone 41-3 as an MS2-polymerase fusion protein was only weak despite insertion into the vector pEX31a (K. Strebel et al. (1985), J. Virology 57, 983–991) in the correct reading frame (checked by sequencing) under the control of the heat-inducible $P_L$ promoter, the insert DNA of the clone 41-3 was used to seek in a λgt10-cDNA bank further positive clones, in order to bring about expression of the latter. The λgt10 bank was produced starting from mRNA of the *P. falciparum* strain SGE2 by the method of T. V. Huynth, R. A. Young and R. W. Davis (in DNA Cloning Vol. I (1985), a practical approach, edited by D. M. Glover, 49–78) and using a 23 bp linker which can be cleaved with the restriction enzymes PstI, NotI and EcoRI. The clone λgt10-41-3 resulted from the screening of this cDNA bank with the insert DNA of the clone 41-3. The insert of this clone was sequenced by the dideoxy chain-termination reaction method of F. Sanger et al. (Proc. Natl. Acad. Sci., U.S.A. 74, 5463–5467 (1977)). The nucleotide sequence of this clone, and the derived amino acid sequence, are depicted in Table 2.

EXAMPLE 4

Expression of the Insert of the Clone λgt10-41-3 in the Vector pEX31

The insert fragment, embracing about 600 bp, of the clone λgt10-41-3 was isolated by gel electrophoresis and was ligated in the vector pEX31b which had been dephosphorylated and digested with the restriction enzyme PstI (T. Maniatis et al. (1982) Molecular cloning, A laboratory manual), and expression was brought about by the method of H. Küpper et al. (in Y. Ikeda and T. Beppu (ed). Proceedings of the Fourth International Symposium on Genetics of Industrial Microorganisms (1982), Kyoto K(o)dansha Ltd., Tokyo), as explained in detail in Example 5. The plasmid pEX31b-41-3 resulting from this expressed the DNA fragment as an MS2 fusion protein in high yield. In this connection there is a discrepancy between the molecular weight of 49 kD determined using SOS gels and the molecular weight of 33 kD predicted on the basis of the length of the coding sequence. This effect is possibly brought about by an unusual SDS-binding behavior because of the histidine/alanine-rich sequence.

EXAMPLE 5

Purification of the Expression Product

A culture of the C600 bacterium which contains the pCI857 plasmid (F. Remaut et al., (1983), Gene 22, 103–113), and had been transformed with the plasmid pEX31b-41-3 was vigorously shaken in 1 l of LB medium containing 50 μg/ml ampicillin and 25 μg/ml kanamycin at 28° C. for 20 h.

After addition of 4 l of LB medium heated to 42° C., the mixture was shaken anew at 42° C. for 4 h. The bacteria were spun down, resuspended in 200 ml of phosphate-buffered saline (PBS) and disrupted mechanically. The soluble proteins were removed by centrifugation, and the sediments, which contained the expression product, were washed twice with PBS and then resuspended in 1M urea. The solubilized proteins were removed by centrifugation, and the sediments were suspended anew in 2M urea. These steps were repeated with increasing urea concentrations. The fusion protein dissolved at a concentration of 7M urea and remained soluble even on dialysis against 2M urea, while contaminating components from *E. coli* precipitated out in this step. The final purity achieved was about 80%.

EXAMPLE 6

Identification of the Corresponding *P. falciparum* Protein

Rabbits were immunized by the following scheme: day 1: 1 mg of purified expression product in complete Freund's adjuvant, subcutaneously; days 2–5, 15–19, 29–33: 0.1 mg of purified expression product, intravenously, on each; day 40: blood sampled.

Mice (Balb/c) which were immunized with the fusion protein received on day 1 0.03 mg of purified expression product in complete Freund's adjuvant subcutaneously, on day 15 0.1 mg in incomplete Freund's adjuvant subcutaneously, and on day 29 0.1 mg subcutaneously, and were exsanguinated on day 36. To obtain schizonts, *P. falciparum* was cultivated in human erythrocytes (W. Trager and J. B. Jensen (1976), Science 193, 673–675) and synchronized by treatment with sorbitol (C. Lambros and J. P. Vanderberg (1979), J. Parasitol. 65, 418–420). The schizonts were enriched to about 90% by flotation in RGelafundin (Braun Melsungen) (in analogy to G. Pasvol et al. (1978), Ann. Trop. Med. Parasitol. 72, 87–88). The schizonts were spun down, washed, dissolved in SDS sample buffer, heated at 100° C. for 5 min., sonicated and frozen in aliquots.

Aliquots of the schizont solution were fractionated by SDS PAGE and transferred to nitrocellulose. The membrane was saturated with 5% skim milk powder in PBS and incubated with suitable dilutions of the antisera for investigation, and then with species-specific biotinylated second antibodies. The bound antibodies were located using avidin/biotin-peroxidase and diaminobenzidine/H$_2$O$_2$.

EXAMPLE 7

Experimental Protection in an Animal Model: Immunization of *Aotus azarae boliviensis* (Karyotype VI)

This experiment was carried out to test the efficacy of the HRPII partial sequence (HRPII-P) with regard to the induction of protective immunity in *P. falciparum*-susceptible monkeys.

1. Design of Experiment 9 healthy aotus monkeys of the abovementioned species (1000–1500 kg body weight, male and female animals bred by Behringwerke AG) were randomized and divided into 3 groups with 3 animals each.

All 3 animals in group A were immunized 3× subcutaneously with 100 μg of the pEX31b-41-3 expression product (dissolved in PBS) each time at intervals of 3 weeks. A 10% admixture of 50% Al(OH)$_3$+45% lecithin+5% saponin to the antigen served as adjuvant. The 3 animals in group B were immunized by the same scheme with an MS2 fusion protein 31-1 longer repeat delete (31-1 lrd), which contains an N-terminal partial sequence of the 200 kD precursor protein of a merozoite surface antigen (U.S. Pat. No. 879,076) and which was obtained analogously.

3 animals in the infection control group each received, likewise according to the abovementioned scheme, an injection composed of PBS+adjuvant without antigenic component.

TABLE 1

```
                 10                          30                          50
CCGTTTTTGCTTCCGTACTTTTGTTAGATAACAATAACTCCGAATTTAACAATAACTTGT
Val Phe Ala Ser Val Leu Leu Leu Asp Asn Asn Asn Ser Glu Phe Asn Asn Asn Leu P 70                          90                         110
TTAGCAAAAATGCAAAAGGACTTAATTCAAATAAGAGATTATTACACGAAAGTCAAGCAC
he Ser Lys Asn Ala Lys Gly Leu Asn Ser Asn Lys Arg Leu Leu His Glu Ser Gln Ala H 130                         150                         170
ATGCAGGTGATGCCCATCATGCACATCATGTAGCTGATGCTCATCATGCTCACCATGCAG
is Ala Gly Asp Ala His His Ala His His Val Ala Asp Ala His His Ala His His Ala A 190                         210                         230
CTAATGCTCACCATGCAGCTAATGCTCACCATGCAGCTAATGCTCATCATGCAGCTAATG
la Asn Ala His His Ala Ala Asn Ala His His Ala Ala Asn Ala His His Ala Ala Asn A 250                         270                         290
CTCACCATGCAGCTAATGCTCATCATGCAGCTAATGCTCGCCATGCAGCTAATGCTCACC
la His His Ala Ala Asn Ala His His Ala Ala Asn Ala Arg His Ala Ala Asn Ala His H 310                         330                         350
ATGCAGCTAATGCTCACCATGCAGCTGATGCTAATCACGGATTTCATTTTAACCTTCACG
is Ala Ala Asn Ala His His Ala Ala Asp Ala Asn His Gly Phe His Phe Asn Leu His A 370                         390                         410
ATAACAATTCCCATACTTTACATCATGCAAAAGCTAATGCTTGTTTTGATGATTCTCACC
sp Asn Asn Ser His Thr Leu His His Ala Lys Ala Asn Ala Cys Phe Asp Asp Ser His H 430                         450                         470
ATGACGATTCCCACCATGATGGAGCACACCACGACGATGCCCACCATGATGGAGCACACC
is Asp Asp Ser His His Asp Gly Ala His His Asp Asp Ala His Hisa Asp Gly Ala His H 490
ACGACGATGCCCACCAT
is Asp Asp Ala His His
```

TABLE 2

```
                 10                          30                          50
CATGTAGCCGATGCCCATCATGCTCATCATGCAGCCGATGCCCATCATGCTCATCATGCA
His Val Ala Asp Ala His His Ala His His Ala Ala Asp Ala His His Ala His His Ala 70                          90                         110
GCCGATGCCCATCATGCTCATCATGCAGCCTATGCCCATCATGCTCATCATGCAGCCGAT
Ala Asp Ala His His Ala His His Ala Ala Tyr Ala His His Ala His His Ala Ala Asp 130                         150                         170
GCCCATCATGCTCATCATGCTCACCATGCAGCCGATGCCCATCACGCTCATCATGCAGCC
Ala His His Ala His His Ala His His Ala Ala Asp Ala His His Ala His His Ala Ala 190                         210                         230
GATGCCCATCATGCTCACCATGCAGCTGATGCTCATCACGCTCATCATGCAGCCGATGCC
Asp Ala His His Ala His His Ala Ala Asp Ala His His Ala His His Ala Ala Asp Ala 250                         270                         290
CATCATGCTCATCATGCAGCCGATGCCCATCATGCTCACCATGCATCCGATGCTCATCAT
His His Ala His His Ala Ala Asp Ala His His Ala His His Ala Ser Asp Ala His His
```

TABLE 2-continued

```
       310                    330                    350
GCAGCTGATGCTCACCATGCAGCCTATGCCCATCATGCTCATCATGCTCATCATGCATCC
Ala Ala Asp Ala His His Ala Ala Tyr Ala His His Ala His His Ala His His Ala Ser 370                    390                    410
GATGCTCATCATGCAGCTGATGCTCACCATGCAGCTTATGCCCATCACGCTCATCATGCA
Asp Ala His His Ala Ala Asp Ala His His Ala Ala Tyr Ala His His Ala His His Ala 430                    450                    470
GCTGATGCTCATCATGCAGCCGATGCCCATCATGCTCACCATGCAACCGATGCTCATCAC
Ala Asp Ala His His Ala Ala Asp Ala His His Ala His His Ala Thr Asp Ala His His 490                    510                    530
GCTCACCATGCAGCCGATGCTCACCATGCAACCGATGCTCACCATGCAGCCGCACACCAC
Ala His His Ala Ala Asp Ala His His Ala Thr Asp Ala His His Ala Ala Ala His His 550                    570
GAAGCCGCCACACATTGCCTACGCCATTAAATTTATTTAATAA
Glu Ala Ala Thr His Cys Leu Arg His End
```

TABLE 3

```
  1 CATGTAGCCGATGCCCATCATGCTCATCATGCAGCCGATGCCCATCATGC  50
    |||| ||||||||||||||||||||||| |||||||| ||||| ||||| ||
354 CATGCAGCCGATGCCCATCATGCTCACCATGCAGCTGATGCTCATCACGC  403

51 TCATCATGCAGCCGATGCCCATCATGCTCATCATGCAGCCTATGCCCATC  100
    ||||||||||||||||||||||||||||||||||||||||||||||||||
404 TCATCATGCAGCCGATGCCCATCATGCTCATCATGCAGCCTATGCCCATC  453

101 ATGCTCATCATGCAGCCGATGCCCATCATGCTCATCATGCTCACCATGCA  150
    ||||||||||||| ||||||| |||||||| | |||||||||||||
454 ATGCTCATCATGCATCCGATGCTCATCATGCAGCTGATGCTCACCATGCA  503

151 GCCGATGCCCATCACGCTCATCATGCAGCCGATGCCCATC.........A  191
    || |||||||||||||||||||||||| ||||| ||||            |
504 GCTTATGCCCATCACGCTCATCATGCAGCTGATGCTCATCATGCAGCTGA  553

192 TGCTCACCATGCAGCTGATGCTCATCACGCTCATCATGCAGCCGATGCCC  241
    |||||||||||||||| |||| ||||||||||||||||||||| ||||| |
554 TGCTCACCATGCAGCTTATGCCCATCACGCTCATCATGCAGCTGATGCTC  603

242 ATC.......:...ATGCTCATCATGCAGCCGATGCCCATCATGCTCACCAT  282
    |||           ||||||| |||||| ||||||| ||||| |||||||||
604 ATCATGCAGCCGATGCTCACCATGCAACCGATGCTCATCACGCTCACCAT  653

283 GCATCCGATGCTCATCATGCAGCTGATGCTCACCATGCAGCCTATGCCCA  332
    ||| ||||||||| |||||| | ||||||||| ||||||| |||| ||
654 GCAGCCGATGCTCACCATGCAACCGATGCTCATCATGCAGCCGATGCTCA  703

333 TCATGCTCATCATGCTCATCATGCATCCGATGCTCATCATGCAGCTGATG  382
    |||||      |||||||||||||| ||||||||||||||||||||  |||
704 CCATGCAGCCGATGCTCATCATGCAACCGATGCTCATCATGCAGCCGATG  753

383 CTCACCATGCAGCTTATGCCCATC.........ACGCTCATCATGCAGCT  423
    |||||||||| |    |||| ||||         | ||||| ||||||||
754 CTCACCATGCAACCGATGCTCATCATGCAGCCGATGCTCACCATGCAGCC  803

424 GATGCTCATCATGCAGCCGATGCCCATCATGCTCACCATGCAACCGATGC  473
    |||||||  |||||| ||||| | |||||  |||||||||||||| |||||||
804 GATGCTCACCATGCAACCGATTCTCATCACGCTCACCATGCAGCCGATGC  853

474 TCATCA....:...CGCTCACCATGCAGCCGATGCT....:........C  502
```

TABLE 3-continued

```
         |||||      |||  |||||||||  |  ||||||                              |
854 TCATCATGCAGCCGCACACCATGCAACTGATGCTCACCATGCAGCCGCAC 903

503 ACCATGCAACCGATGCTCACCATGCAGCCGCACACCACGAAGCCGCCACA 552
    ||||||||||||||||||||||||||||||||||||||||||||||||||
904 ACCATGCAACCGATGCTCACCATGCAGCCGCACACCACGAAGCCGCCACA 953

553 CATTGCCTACGCCATTAAATTTATTTAATAA 583
    |||||||||||||||||||||||||||||||
954 CATTGCCTACGCCATTAAATTTATTTAATAA 984
```

TABLE 4

| Group | Number of aotus | μg of antigen 3 × immuniz. total dose | adjuvant | Challenge infection 55 d. after 1st imm. |
|---|---|---|---|---|
| A HRPII-P | 3 | 300 | modified Al(OH)₃ | 5 × 10⁶ parasit. ery. P. falciparum strain Palo Alto from splenectom. donor monkeys |
| B 31-1 lrd | 3 | 300 | | |
| C infection contr. | 3 | 0 | | |

In order to ensure that the experimental *P. falciparum* infection in the animals was as near equal as possible, all the monkeys were splenectomized (increased susceptibility) six days after the Last immunization. One animal in the control group died intercurrently, as a consequence of the splenectomy, before the malaria infection.

58 days after the 1st vaccination, all the aotus were infected intravenously with $5 \times 10^6$ parasitized erythrocytes. The challenge strain chosen was *P. falciparum* Palo Alto which, adapted in vitro to aotus erythrocytes, was transferred directly from a splenectomized donor animal (16% parasitemia) to the experimental animals. This strain is distinguished by high infectiosity by comparison with other *P. falciparum* subspecies. It is also of interest to mention that this strain is heterologous to the strain SGE-2 (Geneva) used for isolation of the antigen (provenance, serotype, enzyme pattern).

Physiological, parasitological, serological and clinicochemical parameters were investigated throughout the observation study (before and after immunization and after challenge).

2. Results

No pathological changes in any of the physiological (clinical examination, temperature, weight) or clinicochemical (erythrocytes, hematocrit, ESR, serum enzymes GPT and GOT) parameters investigated emerged during the entire immunization period. Additional drug safety investigations (acute subcutaneous toxicity in mice, local tolerability in monkeys as specified in the European Pharmacopoeia) demonstrated that the safety and tolerability of the vaccine preparations used were adequate.

2.1 Parasitemia

The main parameter for assessing the value of induced protection is microscopic detection of parasitized erythrocytes in the peripheral blood of the experimental animals.

Figure 2:
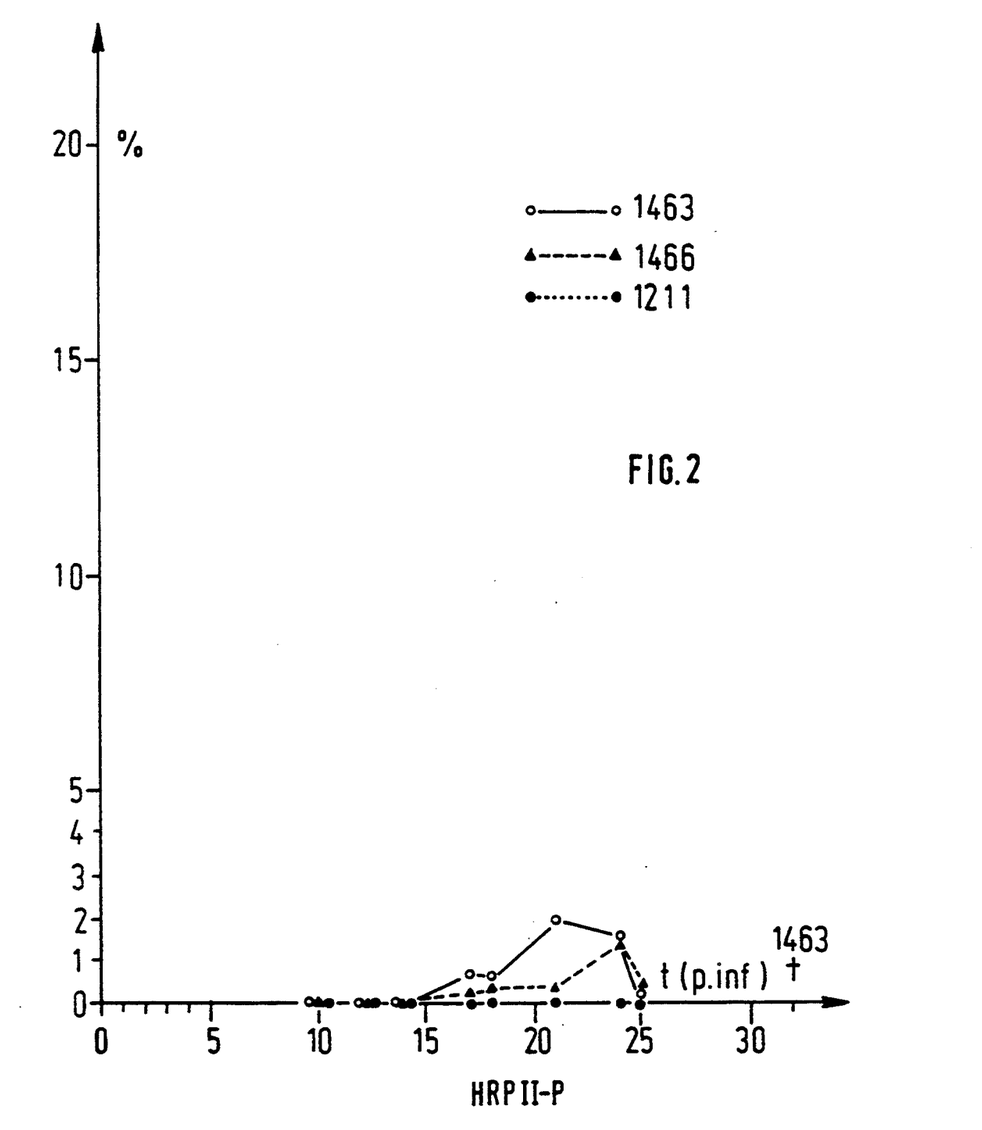

As soon as 7-10 days after infection a few (less than 1 per thousand) parasitized erythrocytes were detected in the Giemsa-stained blood smears from the non-immunized animals and the animals vaccinated with the 31-1 lrd antigen. The appearance of parasites in the animals immunized with the HRPII-Pantigen was delayed to 10-15 days after infection (FIG. 2).

Measured by the degree of parasitemia (as well as by comparison with data known from the literature) all the monkeys immunized with the HRPII-P were protected (not sterile immunity). The parasitemia which occurred after a delay showed maximum levels of 1-2% in 2 animals, which resulted in spontaneous freedom from parasites after 5 days, whereas monkey no. 1211 remained parasitologically negative throughout the observation period apart from a brief parasitemia of 1 per thousand occurring on day 10 after infection (see FIG. 2).

Figure 1:
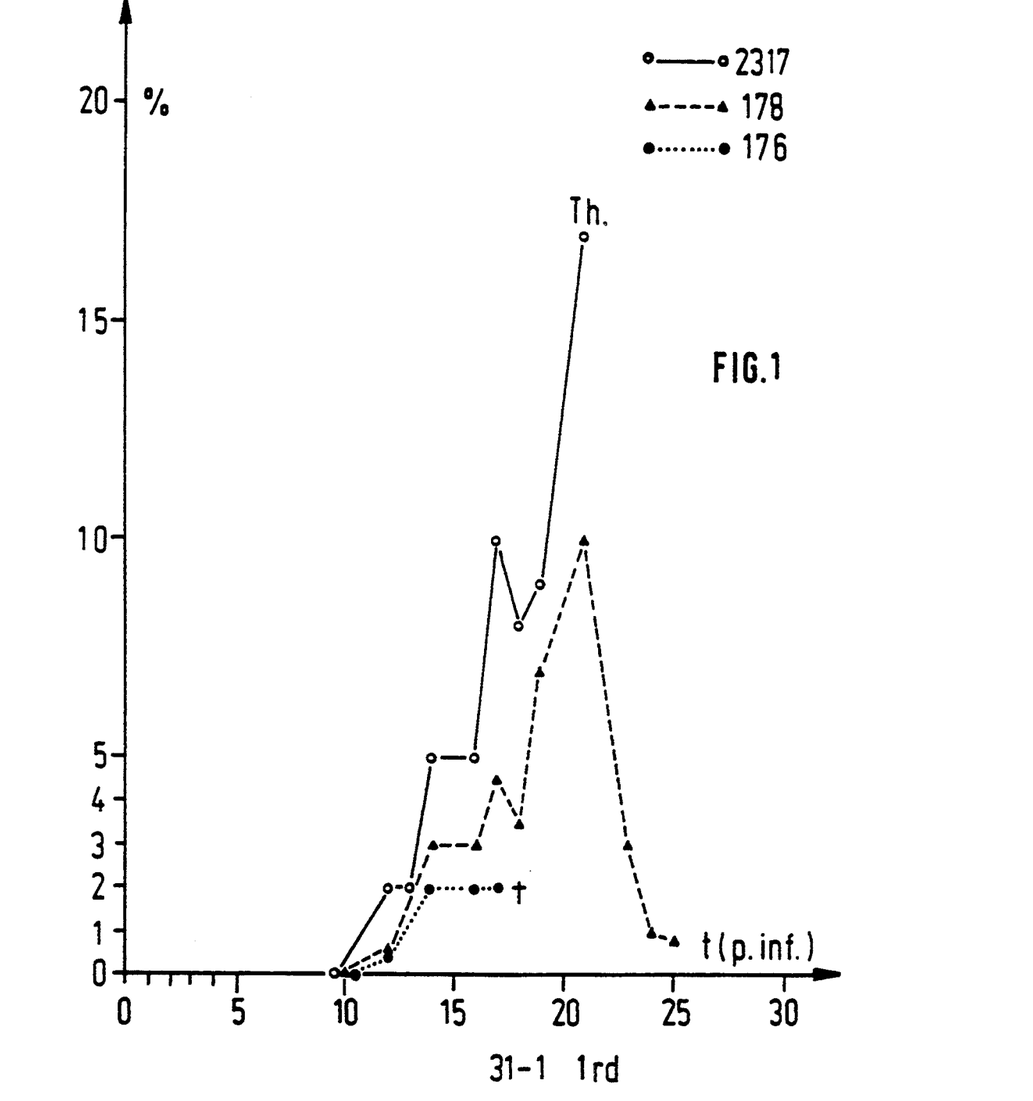

In contrast, the animals immunized with the 31-1 lrd polypeptide were unprotected (FIG. 1). Whereas one animal was able itself to control a maximum parasitemia of 10%, monkey no. 2317 had to be subjected to oral chemotherapy with mefloquine (Hoffmann La Roche) in order to prevent a lethal outcome of the infection. The challenge strain Palo Alto had proved to be chloroquine-resistant in previous infection experiments.

The non-immunized (control) monkeys (FIG. 3) showed maximum parasitemias of between 3 and 8%, and these, compared with the rapidly diminishing parasitemia of the HRPII-P immunized animals were not controlled without therapy until 15 days had elapsed.

Figure 3:
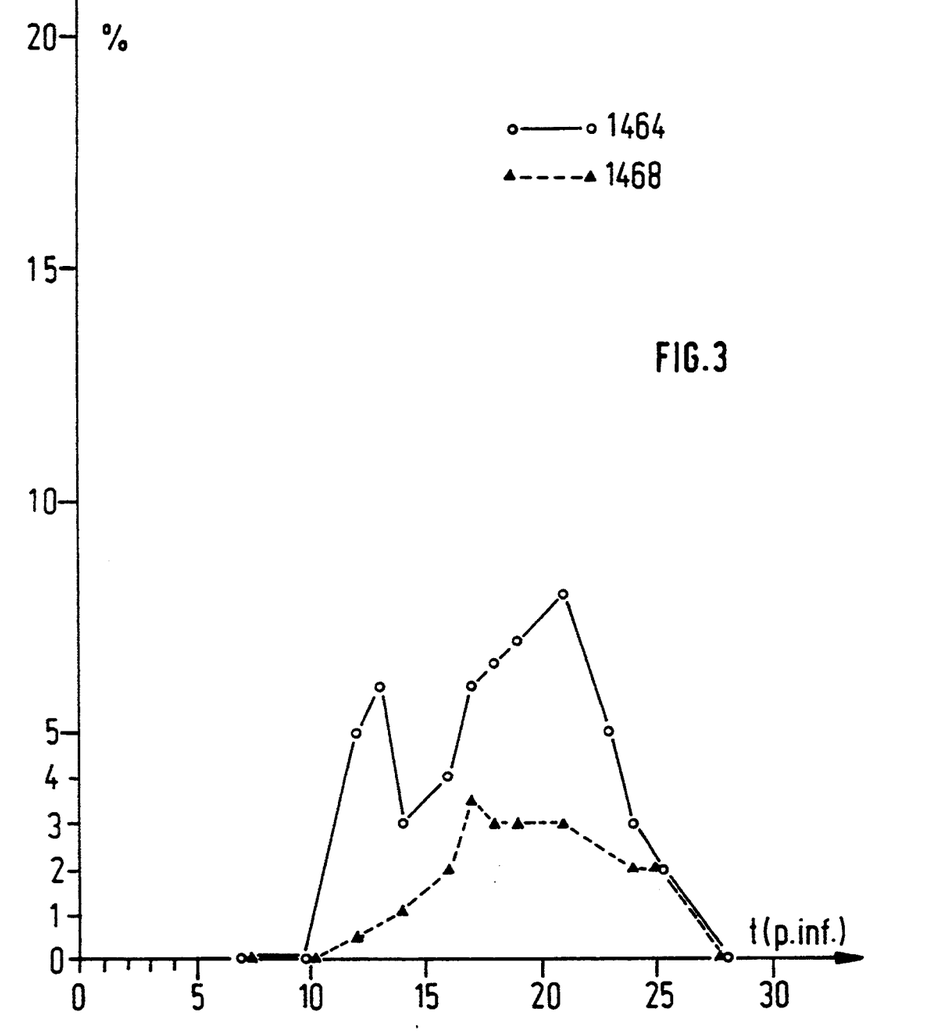
FIG. 3: Controls

The relative number of infected erythrocytes (=% parasitemia) is plotted on the ordinate in each of FIGS. 1 to 3. The abscissa represents the time axis (=days after infection).

2.2 Serology

Antibodies against the immunizing antigens were determined using an ELISA. 96-Well polystyrene plates were coated with the 31-1 lrd and HRPII-P fusion proteins and incubated with the sera from the immunized monkeys (diluted 1:100); after washing to remove unbound reactants, specific antibodies were detected with peroxidase-labeled rabbit antihuman IgG.

The malaria-specific immune response was also checked and confirmed by indirect immunofluorescence. Acetone-fixed *P. falciparum*-infected human erythrocytes were incubated with serial dilutions of the sera for investigation, and the binding of specific antibodies was visualized with FITC-labeled rabbit antihuman IgG.

All immunized animals showed seroconversion due to the formation of specific antibodies, and this was detected with both serological methods. Only the antibodies directed against the HRPII-P antigen showed a correlation with the protection, whereas the 31-1 lrd polypeptide proved to be only a strong immunogen without inducing a protective action. The results of the parasitological and serological investigations are compiled in Tab. 5.

TABLE 5

Parasitological and serological findings in aotus immunized with recombinant polypeptides HRPII-P and 31-1 lrd antigen from *P. falciparum*

| Aotus No. | Antigen | Max. parasitemia % infect. days erythr. | after challenge | Serology on day of infect. IFT | ELISA 37 kD | ELISA 31-1 lrd |
|---|---|---|---|---|---|---|
| 1211 | HRPII-P | 1% | 10 | 1:80 | 0.6 | n.d. |
| 1466 | | 1.5 | 24 | 1:40 | 0.5 | n.d. |
| 1463 | | 2 | 21 | 1:40 | 0.6 | n.d. |
| 2317 | 31-1 lrd | 17 | 21 | 1:10 | n.d. | 0.6 |
| 178 | | 10 | 21 | 1:80 | n.d. | 0.8 |
| 176* | | 2 | 17 | 1:320 | n.d. | 0.7 |
| 1468 | infect. | 4 | 17 | neg. | 0.03 | 0.02 |
| 1464 | control | 8 | 21 | neg. | 0.03 | 0.03 |

*)died intercurrently on day 17 after infection (peritonitis)
**)one animal died from consequences of the splenectomy before infect.
n.d.: not done

BRIEF DESCRIPTION OF THE DRAWINGS

FIGS. 1 to 3: Course of parasitemia in aotus monkeys immunized with the recombinant proteins 31-1 lrd (FIG. 1) or HRPII-P (FIG. 2).

The y-axis of each figure shows the percentage of infected erythrocytes; the x-axis shows the days post-infection.

We claim:

1. A method of inducing partial immunological protection against *P. falciparum* blood stage infection in a patient, comprising administering an isolated or purified HRP-II antigen of *P. falciparum* comprising the amino acid sequence as shown in Table 2 in the form of a vaccine in an amount sufficient to reduce the severity of infection by *P. falciparum*.

2. A vaccine comprising a pharmaceutically acceptable adjuvant and an isolated or purified *P. falciparum* HRP-II antigen, wherein said antigen comprises the following amino acid sequence:

```
                10                          30                          50
CAT GT AGCCGAT GCCCAT CAT GCT CAT CAT GCAGCCGAT GCCCAT CAT GCT CAT CAT GCA
His Val Ala Asp Ala His His Ala His His Ala Ala Asp Ala His His Ala His His Ala
                70                          90                         110
GCCGAT GCCCAT CAT GCT CAT CAT GCAGCCT AT GCCCAT CAT GCT CAT CAT GCAGCCGAT
Ala Asp Ala His His Ala His His Ala Ala Tyr Ala His His Ala His His Ala Ala Asp
               130                         150                         170
GCCCAT CAT GCT CAT CAT GCT CACCAT GCAGCCGAT GCCCAT CACGCT CAT CAT CAGGCC
Ala His His Ala His His Ala His His Ala Ala Asp Ala His His Ala His His Ala Ala
               190                         210                         230
GAT GCCCAT CAT GCT CACCAT GCAGCT GAT GCT CAT CACGCT CAT CAT GCAGCCGAT GCC
Asp Ala His His Ala His His Ala Asp Ala His His Ala His His Ala Ala Asp Ala
               250                         270                         290
CAT CAT GCT CAT CAT GCAGCCGAT GCCCAT CAT GCT CACCAT GCAT CCGAT TGCCAT CAT
His His Ala His His Ala Ala Asp Ala His His Ala His His Ala Ser Asp Ala His His
               310                         330                         350
GCAGCT GAT GCT CACCAT GCAGCCT AT GCCCAT CAT GCT CAT CAT GCT CAT CAT GCATCC
Ala Ala Asp Ala His His Ala Ala Tyr Ala His His Ala His His Ala His His Ala Ser
               370                         390                         410
GAT GCT CAT CAT GCAGCT GAT GCT CACCAT GCAGCTT AT GCCCAT CACGCT CAT CAT GCA
Asp Ala His His Ala Ala Asp Ala His His Ala Ala Tyr Ala His His Ala His His Ala
               430                         450                         470
GCT GAT GCT CAT CAT GCAGCCGAT GCCCAT CAT GCT CACCAT GCAACCGAT GCT CAT CAC
Ala Asp Ala His His Ala Ala Asp Ala His His Ala His His Ala Thr Asp Ala His His
               490                         510                         530
GCT CACCAT GCAGCCGAT GCT CACCAT GCAACCGAT GCT CACCAT GCAGCCGCACACCAC
Ala His His Ala Ala Asp Ala His His Ala Thr Asp Ala His His Ala Ala Ala His His
               550                         570
GAAGCCGCCACACATT GCCT ACGCCATT AAATT ATTT AATAA
Glu Ala Ala Thr His Cys Leu Arg His End
```

* * * * *

UNITED STATES PATENT AND TRADEMARK OFFICE
CERTIFICATE OF CORRECTION

PATENT NO. : 5,393,523
DATED : February 28, 1995
INVENTOR(S) : Bernhard Knapp et al.

It is certified that error appears in the above-indentified patent and that said Letters Patent is hereby corrected as shown below:

On the title page, item [54]:

-- RECOMBINANT HISTIDINE-RICH PROTEIN OF PLASMODIUM FALCIPARUM, ITS PREPARATION AND USE --

Item [75] Inventors, line 4, "Hans Kupper" should read -- Hans Küpper --.
Claim 2, columns 11-12, in the sequence listing, line 9, last 9 letters in line, below number "290" and above "Ala His His", "TGCCATCAT" should read --GCTCATCAT-- second to last line of sequence listing, below number "570", after "AAA", "TT" should read --TTT---.

Signed and Sealed this

Twelfth Day of September, 1995

*Attest:*

BRUCE LEHMAN

*Attesting Officer*  *Commissioner of Patents and Trademarks*